United States Patent [19]
Asai et al.

[11] Patent Number: 4,905,293
[45] Date of Patent: Feb. 27, 1990

[54] IMAGE INPUT DEVICE

[75] Inventors: Ko Asai; Koichiro Morita, both of Tokyo, Japan

[73] Assignee: NEC Corporation, Tokyo, Japan

[21] Appl. No.: 326,426

[22] Filed: Mar. 22, 1989

Related U.S. Application Data

[63] Continuation of Ser. No. 142,279, Jan. 4, 1988, abandoned, which is a continuation-in-part of Ser. No. 943,877, Dec. 19, 1986, abandoned, which is a continuation-in-part of Ser. No. 755,575, Jul. 16, 1985, abandoned.

[30] Foreign Application Priority Data

Jul. 18, 1984 [JP] Japan ............................ 59-148890
Jul. 18, 1984 [JP] Japan ............................ 59-148891

[51] Int. Cl.4 ............................................. G06K 9/32
[52] U.S. Cl. ........................................ 382/4; 356/71
[58] Field of Search ................. 382/4, 5, 65; 356/71; 15/250 R, 250.02, 250.03, 250.22

[56] References Cited

U.S. PATENT DOCUMENTS 3,482,498 12/1969 Becker ................................. 382/4
3,677,623 7/1972 Hall et al. .......................... 356/71
3,716,301 2/1973 Caulfield et al. ................... 356/71
3,947,128 3/1976 Weinberger et al. ................ 382/4
4,120,585 10/1978 De Palma et al. .................. 356/71
4,455,083 6/1984 Elmes ................................. 382/4

Primary Examiner—Leo H. Boudreau
Attorney, Agent, or Firm—Foley & Lardner, Schwartz, Jeffery, Schwaab, Mack, Blumenthal & Evans

[57] ABSTRACT

An image input device for optically sensing a fingerprint or like pattern to convert it to an electrical signal is disclosed. A guide is provided on a contact surface, or reflective surface, of a prism to orient the lengthwise direction of the pattern of an object parallel to a ridge, which is defined by an incidence surface and a wayout surface of the prism.

16 Claims, 3 Drawing Sheets

IMAGE INPUT DEVICE

This application is a continuation of application Ser. No. 07/142,279, filed Jan. 4, 1988 now abandoned; which is a continuation of application Ser. No. 06/943,877, filed Dec. 19, 1986, now abandoned; is a continuation of application Ser. No. 06/755,575, filed July 16, 1985, now abandoned.

BACKGROUND OF THE INVENTION

The present invention relates to an image input device and, more particularly, to an image input device for optically sensing fingerprints and other patterns to convert them to electrical signals.

Implementations available today for identifying humans and distinguishing them from one another include a system which relies on fingerprints. By virtue of the idosyncrasy and invariability of fingerprints and aided by pattern recognition technology, such an identification system compares characteristics, or minutiae, of fingerprints with those of registered fingerprints for similarities.

In a device based on the above-mentioned identification principle, a finger is laid on a predetermined contact surface of a glass prism and illuminated by light from behind the contact surface, so that the light reflected from the contact surface is converted to an electrical signal representative of a pattern peculiar to the fingerprint. This kind of pattern collection utilizes optical boundary changes of glass which occur at the contact surface of the prism due to the fingerprint pattern. Changes in the intensity of reflected light due to the optical boundary changes are picked up by an industrial television (ITV) camera or like imaging apparatus to provide a photoelectrically converted image of the fingerprint pattern. The described type of apparatus is disclosed in Japanese Patent Disclosure Nos. 54-69300 and 54-85600, for example.

The prism in any of the prior art apparatuses mentioned above has an incidence surface to which light from a light source is incident, a reflective surface for reflecting the incident light and on which a finger is laid, and a wayout surface through which light from the reflective surface emerges to the outside. In this condition, the lengthwise direction of the pattern of the fingerprint (identical with the lengthwise direction of the finger) is positioned substantially perpendicular to the ridge which is defined by the incidence and wayout surfaces of the prism. This brings about a problem that due to the triangular cross-section of the prism the image pattern coming out of the wayout surface to be picked up by the camera is blurred at both ends portions with respect to the lengthwise direction.

SUMMARY OF THE INVENTION

It is therefore an object of the present invention to provide an image input device which frees an image picked up from blurring due to the triangular cross-section of a prism to thereby offer a clear-cut image.

It is another object of he present invention to provide an image input device which facilates positioning of an object on a contact surface of a prism to eliminate blurring of an image picked up.

It is another object of the present invention to provide a generally improved image input device.

An image input device for optically sensing a pattern of an object to convert the pattern to an electrical signal for examination of the present invention comprises a prism having three discrete surfaces which comprise an incidence surface to which light is incident, a reflective surface for reflecting light which is incident to the incidence surface and on which the object is to be laid, and a wayout surface through which light reflected by the reflective surface comes out, a light source for irradiating the incidence surface of the prism, and a guide for causing a lengthwise direction of the pattern of the object to extend substantially in alignment with a direction which is parallel to a ridge defined by the incidence surface and the wayout surface of the prism.

In accordance with the present invention, an image input device for optically sensing a fingerprint or like pattern to convert it to an electrical signal is disclosed. A guide is provided on a contact surface, or reflective surface, of a prism to orient the lengthwise direction of the pattern of an object parallel to a ridge, which is defined by an incidence surface and a wayout surface of the prism.

The above and other objects, features and advantages of the present invention will become more apparent from the following detailed description taken with the accompanying drawings.

DESCRIPTION OF THE PREFERRED EMBODIMENTS

While the image input device of the present invention is susceptible of numerous physical embodiments, depending upon the environment and requirements of use, substantial numbers of the herein shown and described embodiments have been made, tested and used, and all have performed in an eminently satisfactory manner.

Figure 1A:
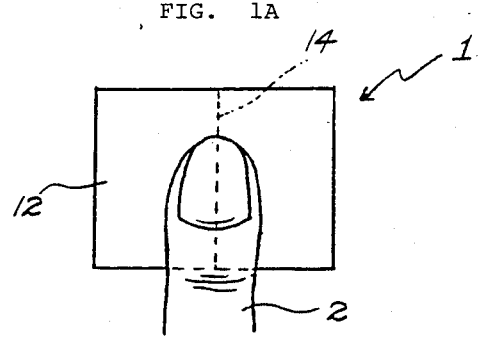
FIG. 1A is a plan view showing a positional relationship between a prism in accordance with the present invention and a finger which is an object to be examined.
Figure 1B:
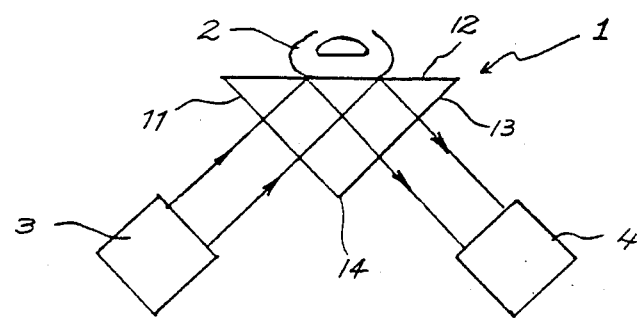
FIG. 1B shows the relationship of FIG. 1A in a front view.
Figure 1C:
FIG. 1C is a view of an exemplary image pattern picked up in accordance with the present invention.

Referring to FIGS. 1A and 1B of the drawings, a prism 1 has an incidence surface 11, a contact surface (reflective surface) 12 on which a finger 2 is laid, and a wayout surface 13. Light issuing from a light source 3 to incident to the incidence surface 11 of the prism 1 illuminates the finger 2 from below the contact surface 12. Then reflected by the surface 12, the light is routed to the outside through the wayout surface 13 to be picked up by a camera 4. The finger 2 is laid on the contact surface 12 of the prism 1 in such orientation that the lengthwise direction of a fingerprint pattern is substantially parallel to a ridge 14, which is defined by the conjugate surfaces 12 and 13 of the prism 1. Such a positional relationship makes it possible to eliminate blurring of an image heretofore caused by the particular configuration of the prism 1 at longitudinally opposite end portions of the pattern, as shown in FIG. 1C. Hence, the signal processing step for digitizing an image pattern signal output from by the camera 4 and that for extracting characteristics of the fingerprint, or minutiae, will be freed from errors so as to promote accurate detection of the characteristics.

Preferred embodiments of the image input device embodying the present invention are shown in FIGS. 2-6. All of these embodiments include guide means for allowing an object, or finger, to be positioned on the contact surface 12 of the prism 1 such that the lengthwise extension of the fingerprint pattern sustantially aligns with the extension of the ridge 14 of the prism 1.

Figure 2A:
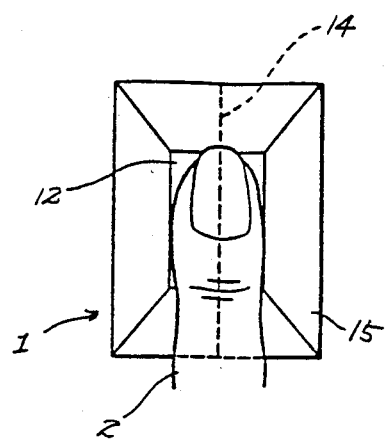
FIG. 2A is a plan view of an image input device embodying the present invention.
Figure 2B:
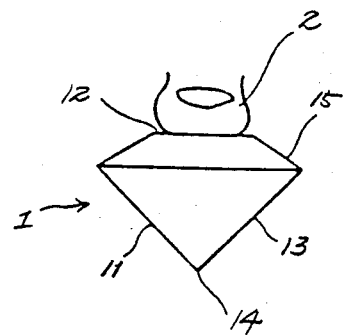
FIG. 2B is a front view of the device shown in FIG. 2A.

Referring to FIGS. 2A and 2B, the prism 1 is cut along all the four edges of the contact surface 12 to provide inclined cut surfaces 15. In this configuration, the surface 12 surrounded by the cut surfaces 15 lies above the other surfaces. The surface 12 has a rectangular configuration such that the lengthwise direction of the finger 2 on the surface 12 is positioned substantially in alignement with the direction of the ridge 14, that is, such that the longer sides of the rectangle defined by the cut surfaces 15 extend parallel to the ridge 14. If desired, however, the prism 1 may be cut along only three sides of the contact surface 12 while leaving the side where the finger 2 is inserted left uncut.

Figure 3A:
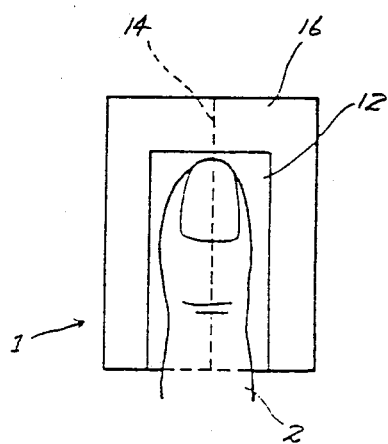
FIG. 3A is a front view of another embodiment of the present invention.
Figure 3B:
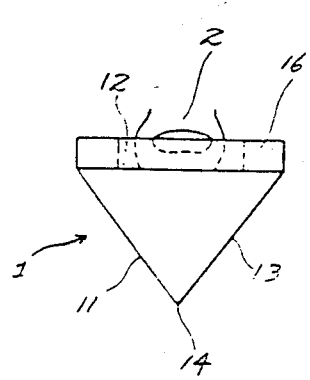
FIG. 3B is a front view of the device shown in FIG. 3A.

Referring to FIGS. 3A and 3B, the prism 1 is provided with conjugate projections 16 which extend along thee sides of the contact surface 12 other than the side through which the finger 2 is to be inserted. The longer sides of the rectangle defined by the projections 16 extend parallel to the ridge 14.

Figure 4:
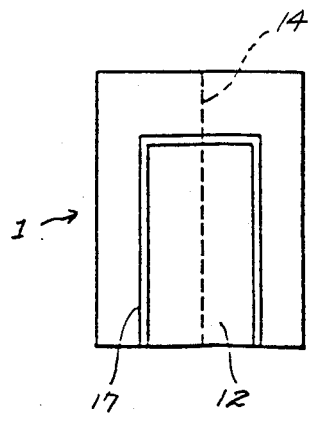
FIGS. 4–6 are plan views showing other various embodiments of the present invention.

Referring to FIG. 4, the contact surface 12 of the prism 1 is provided with a narrow recess or groove 17 which is configured to define a rectangle. Again, the longer sides of the rectangle are oriented parallel to the ridge 14.

Figure 5:
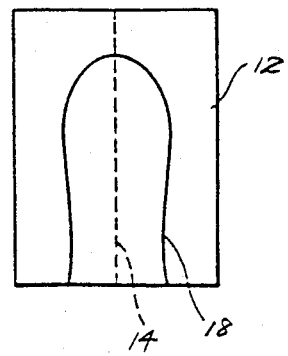

Referring to FIG. 5, a shape representative of a finger is provided by a line 18 which is printed on the contact surface 12 of the prism 1. This will also allow the finger to be positioned such that its lengthwise axis aligns with the ridge 14.

Figure 6:
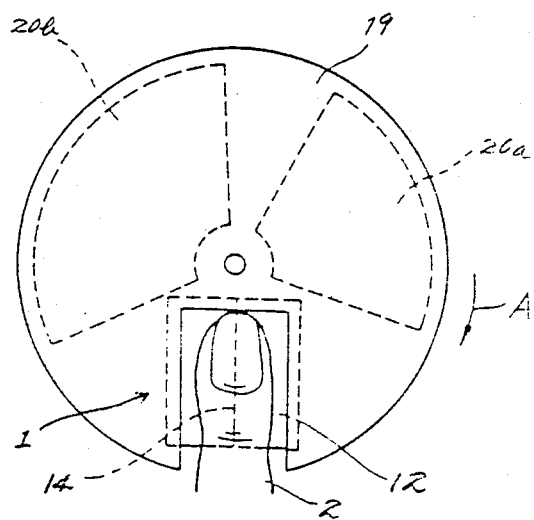

Referring to FIG. 6, still another embodiment of the present invention is shown in which the guide for positioning the finger 2 is implemented with a notch formed in a turntable 19, which is adapted to clean the prism 1. Specifically, a piece of wet cloth 20a and a piece of dry cloth 20b each having a sectorial shape are adhered to that face of the turntable 19 which faces the contact surface 12 of the prism 1 while the turntable 1 is rotated. The wet cloth 20b impregnated with cleaning liquid. After the finger 2 has been removed from the contact surface 12, the turntable 19 is rotated as indicated by an arrow A so that the wet clotch 20a wipes the contact surface 12 and, then, the dry clotch 20b wipes it to remove the cleaning liquid together with impurities. The turntable 19 is stopped immediately before the notch is brought into alignment with the prism 1, that is, in a position where a part of the turntable 19 just ahead of the notch has cover the prism 1. Thereafter, when the next person enters his or her identification (ID) number through a keyboard (not shown), the turntable 19 will be rotated again until it stops in the illustrated position.

In FIG. 6, the notch of the turntable 19 has a rectangular shape the longer sides of which extend parallel to the ridge 14 of the prism 1 in the illustrated position. Such a configuration allows one to successfully lay the finger through the notch of the turntable 19 on the contact surface 12 of the prism 1 such that the lengthwise direction of the fingerprint pattern is aligned with the ridge 14.

While a "live print" has been shown and described as a pattern to be taken, it may be replaced by an opaque fingerprint or a similar transparency which may be implemented, for example, by a thin plastic film.

In summary, it will be seen that the present invention provides an image input device which includes a guide so arranged as to cause the lengthwise direction of the pattern of a desired object to be positioned parallel to a ridge between incidence and wayout surfaces of a prism on a contact surface, which is a reflective surface of the prism. Hence, one needs only to put his or her finger or like object on the contact surface of the prism along the guide. Such not only eliminates blurring otherwise occurring at longitudinally opposite end portions of the image to thereby allow a clear-cut pattern to be collected but also facilitates accurate positioning of the object on the contact surface.

Various modifications will become possible for those skilled in the art after receiving the teachings of the present disclosure without departing from the scope thereof.

What is claimed is:

1. An image input device for optically sensing a pattern of an object to convert the pattern to an electrical signal for examination, consisting essentially of a single prism wherein:

said single prism has three discrete surfaces which comprise an incidence surface to which light is incident, a reflective surface for reflecting light which is incident to said incidence surface and on which the object is to be laid, and a way-out surface through which light reflected by said reflective surface comes out;

said image input device further comprising:

a light source for irradiating said incidence surface of the prism; and non-movable guide means fixed to said reflective surface and having a fixed configuration, for causing a lengthwise direction of the pattern of the object to extend substantially in alignment with a direction which is parallel to a ridge defined by the incidence surface and the wayout surface of the prism.

2. An image input device as claimed in claim 1, wherein the guide means comprises inclined cut surfaces provided by cutting edge portions of the reflective surface of the prism on the reflective surface, and a rectangular flat surface surrounded by said inclined cut surfaces, said flat surface being higher in level than the other surfaces and having long sides extending parallel to said ridge.

3. An image input device as claimed in claim 1, wherein the guide means comprises projections which extend on the reflective surface of the prism along sides of the reflective surface except for a side through which the object is to be inserted.

4. An image input device as claimed in claim 1, wherein the guide means comprises an elongate recess which extends in the reflective surface of the prism along edges of the reflective surface, said recess defining a rectangle long sides of which extend parallel to said ridge.

5. An image input device as claimed in claim 1, wherein the guide means comprises a line which is printed on the reflective surface of the prism to represent a contour of the object such that a lengthwise axis of the object substantially aligns with said ridge.

6. An image input device for optically sensing a pattern of an object to convert the pattern to an electrical signal for examination, comprising:
   (a) a prism having three discrete surfaces which comprise
      (1) an incidence surface to which light is incident,
      (2) a reflective surface for reflecting light which is incident on said reflective surface, said reflective surface having an upper contact surface on which the object is to be laid, and
      (3) a wayout surface through which light reflected by said reflective surface comes out;
   (b) a light source for irradiating said incidence surface of the prism;
   (c) a turntable positioned adjacent to and above said contact surface; and
   (d) said turntable having a notched area defining guide means for causing a lengthwise direction of the pattern of the object to extend substantially in alignment with a direction which is parallel to a ridge defined by the incidence surface and the wayout surface of the prism.

7. An image input device as recited in claim 6, wherein said notched area has a rectangular shape with longer sides of said rectangular shape extending parallel to said ridge.

8. An image input device as recited in claim 6, wherein said device further comprises:
   means fixed to said turntable for cleaning said contact surface,
   means fixed to said turntable for drying said contact surface, and
   said turntable rotatable for alternately moving said cleaning means and said drying means across said contact surface and for subsequently positioning said notched area above said contact surface.

9. An image input device as recited in claim 8, wherein said cleaning means includes a cloth impregnated with cleaning fluid.

10. An image input device as recited in claim 8, wherein said drying means includes a dry cloth.

11. An image input device as recited in claim 7, wherein said device further comprises:
    means fixed to said turntable for cleaning said contact surface,
    means fixed to said turntable for drying said contact surface, and
    said turntable rotatable for alternately moving said cleaning means and said drying means across said contact surface and for subsequently positioning said notched area above said contact surface.

12. An image input device as recited in claim 11, wherein said cleaning means includes a cloth impregnated with cleaning fluid.

13. An image input device as recited in claim 11, wherein said drying means includes a dry cloth.

14. An image input device as recited in claim 12, wherein said drying means includes a dry cloth.

15. An image input device as recited in claim 6 further including means for receiving said light from said wayout surface and for converting said received light into said electrical signal.

16. An image input device as recited in claim 8 further including means for receiving said light from said wayout surface and for converting said received light into said electrical signal.

* * * * *